United States Patent [19]
Haber

[11] Patent Number: 5,859,198
[45] Date of Patent: Jan. 12, 1999

[54] PLANT PROTEINS

[76] Inventor: Meir Haber, 5 Hakalanit Street, Netanya 42225, Israel

[21] Appl. No.: 522,179

[22] Filed: Aug. 31, 1995

[30] Foreign Application Priority Data

Sep. 12, 1994 [IL] Israel .................................. 110938

[51] Int. Cl.$^6$ .................................................. C07K 14/405
[52] U.S. Cl. ............................ 530/370; 530/371; 530/379
[58] Field of Search .................................... 530/370, 371, 530/379

[56] References Cited

U.S. PATENT DOCUMENTS

| | | | |
|---|---|---|---|
| 5,015,677 | 5/1991 | Benedict | 524/17 |
| 5,202,236 | 4/1993 | Maugh | 435/69.1 |

FOREIGN PATENT DOCUMENTS

| | | |
|---|---|---|
| 099758 | 7/1984 | European Pat. Off. . |
| 244688 | 5/1987 | European Pat. Off. . |
| 227955 | 11/1987 | European Pat. Off. . |
| 645149 | 3/1995 | European Pat. Off. . |
| 106931 | 3/1992 | Israel . |
| 90/04963 | 5/1991 | WIPO . |

OTHER PUBLICATIONS

Note: Work of Adhesion of Synthetic Polypeptides Containing L–Lysine, *Journal of Colloid and Interface Science*, (1993), v. 156, pp. 515–517.

Round, F. E., *The Ecology of Algae*, (1981), Cambridge University Press, pp. 76–77, 128–129, 298–299.

Marumo, K., et al., Optimization of hydroxylation of tyrosine and tyrosine–containing peptides by mushroom tyrosinase, *Biochima et Biophysica Acta*, (1986), v. 872, pp. 98–103.

Wagner, V.T., et al., Role of a vitronectin–like molecule in embryo adhesion on the brown alga Fucus, *Proc. Natl. Acad. Sci. USA*, (1992), v. 89, pp. 3644–3648.

Waite, J.H., Mini Review: The phylogeny and chemical diversity of quinone–tanned glues and varnishes, *Comp. Biochem. Physiol.*, (1990), v. 97B N. 1, pp. 19–29.

Saez, C., et al., Immunological studies of the polyphenolic proteins of mussels, *Comp. Biochem, Physiol.*, (1991), v. 98B., N. 4, pp. 569–572.

Zhu, J.K., et al., A higher plant extracellular vitronectin–like adhesion protein is related to the translational elongation factor–1a, *The Plant Cell*, (1994), v. 6, pp. 393–404.

Yamada, K.M., Adhesive Recognition Sequences, *The Journal of Biological Chemistry*, (1991), v. 266, N. 20, pp. 12809–12812.

Murray, S.N., et al., The rhodophyta: Some aspects of their biology. III, *Oceanogr. Mar. Biol. Annu. Rev.*, (1992) v. 30, pp. 1–13, 20, 137.

Ruoslahti, E., et al., Anchorage dependence, integrins, and apoptosis, *Cell*, (1994) v. 77, pp. 477–478.

Miyazaki, K., et al., Physarum Vitronectin–like protein: An Arg–Gly–Asp–Dependent–Cell–Spreading Protein with a Distinct NH2–Terminal Sequence, *Experimental Cell Research*, (1993) 106–110.

Alon, R., et al., Streptavidin blocks immune reactions mediated by fibronectin–VLA–5 recognition through an Arg–Gly–Asp mimicking site, *Eur. J. Immunol.*, (1993) v. 23, pp. 893–898.

Doss, R.P., et al., Adhesion of germlings of Botrytis cinerea, *Applied and Environmental Microbiology*, (1995) V. 61, pp. 260–265.

Shimizu, Y., Microalgal metabolites, *Chem. Rev.*, (1993) V. 93, N. 5, pp. 1685–1686.

Huber, O., et al., Algal–CAMs: isoforms of a cell adhesion molecule of the alga Volvox with homology to Drosophila fascilin I, *The EMBO Journal*, (1994) V. 13, N. 18, pp. 4212–4222.

Molina, M.C., et al., Enzymatic activities of algal–binding protein and its algal cell wall receptor in the lichen Xanthoria parietina . . . *Plant Physiol. Biochem.*, (1993) 31(2) pp. 131–133.

Chamberlain, A.H.L., et al., Aspects of spore production in the red alga Ceramium, *Protoplasma*, (1973) V. 76, pp. 139–159.

Schindler, M., et al., RGD–dependent linkage between plant cell wall and plasma membrane: consequences for growth, *The Journal of Cell Biology*, (1989) V. 108, p. 1955.

Kitagaki–Ogawa, H., Diversities in animal vitronectins. Differences in molecular weight, immunoreactivity and carbohydrate chains, *Biochimica et Biophysica Acta*, (1990) V. 1033, pp. 49–56.

Brown, M.R., The amino–acid and sugar composition of 16 species of microalgae used in mariculture, *J. Exp. Mar. Biol. Ecol.*, (1991) V. 145, pp. 79–99.

Knox, P., Emerging patterns of organization at the plant cell surface, *Journal of Cell Science*, (1990) V. 96, pp. 557–561.

J. Phycol. Supplement 31(3), (Jun. 1985), Abstract Nos. 7,8,9.

Quatrano, R.S., Mechanism of cytoplasmic localization, identifying no. 9318757. (abstract). (1993).

Apple, M.E., et al., Inhibition of tetraspore adhesion in Champia parvula (Rhodophyta), *Phycologia*, (1995), vol. 34(5), pp. 417–423.

Gupta, Medune AN #/ 91219713, (1991).

Holbrook, Biosis AN #/ 88:248357, (1988).

Bell, Caplus AN #/ 1986:31175, (1985).

Lisboa, Biosis AN #/ 83:287023, (1982).

Targett, Biosis AN #/80:179589, (1979).

(List continued on next page.)

Primary Examiner—Cecilia J. Tsang
Assistant Examiner—Patrick R. Delaney
Attorney, Agent, or Firm—Welsh & Katz, Ltd.

[57] ABSTRACT

Adhesive proteins isolated from mature plants selected from the group consisting of macroalgae and microalgae, said proteins being characterized by the presence of at least one RGD or RGD-like or other adhesive recognition sequence, the absence of DOPA and hydroxyproline units, and by the fact that the proteins may be used by the plants in their natural state, for the purpose of adhesion to substrates.

20 Claims, No Drawings

OTHER PUBLICATIONS

Darryl L. Kropf, Induction of Polarity In Fucoid Zygotes, The Plant Cell, vol. 9, 1011–1020, Jul. 1997, American Society of Plant Physiologists.

Luis O. Burzio, et al., Environmental Bioadhesion: Themes and Applications, Environmental Biotechnology, vol. 8, pp. 309–312, 1997.

C.A. Henry, et al., Localized Membrane–Wall Adhesions in Pelvetia Zygotes, Protoplasma (1996) 190: pp. 39–52.

Susan G. Kaminsky, et al., Integrin and Spectrin Homologues, and Cytoplasm–Wall Adhesion in Tip Growth, Journal of Coll Science 108, 849–856, 1995.

Lisboa et al., The Trace Sterols of the Red Alga Laurencia Papillosa Investigated by Open tubular Capillary Column Gas Chromatography–Mass Spectrometry, Comp Biochem Physiol.B Comp, Biochem., vol. 73B, No. 2., 1982, pp. 257–264.

Holbrook et al., Photosynthesis in Marine Macroalgae: Evidence for Carbon Limitation, Can. J. Bot., vol. 66, 1988, pp. 577–582.

S. Beer and A. Eshel, Determining Phycoerythrin and Phycocyanin Concentrations in Aqueous Crude Extracts of Red Algae, Aust. J. Mar. Freshw. Res., vol. 36, 1985, pp. 785–792.

M. Targett and A. Mitsui, Toxicity of Subtropical Marine Algae Using Fish Mortality and Red Blood Cell Hemolysis for Bioassays, J. Phycol. vol. 15, 1979, pp. 181–185.

Vreeland, Valerie and Lynn Epstein, Analysis of Plant–Substratum Adhesives, Modern Methods of Plant Analysis, vol. 17, pp. 95–116.

Tamarron Meeting Report, The Plant Extracellular Matrix: News From The Cell's Frontier, Sep. 1996, pp. 1451–1463.

M.R. Gretz, et al., Cell Wall Composition Of The Conchocelis Phases Of Bangia atropurpurea And Porphyra leucosticta (Rhodophyta), Botanica Marina vol. XXIX,, pp. 91–96, 1986.

Leonard S. Mukai, et al., Chemical Composition And Structure Of The Cell Walls Of the Conchocelis And Thallus Phases of Porphyra Tenera (Rhodophyceae), J. Phycol. vol. 17, pp. 192–198, 1981.

Ralph S. Quatrano, et al., Role Of The Cell Wall In The Determination Of Cell Polarity And The Plane Of Cell Division In Fucus Embryos, Elsevier Science Ltd., vol. 2, No. 1, pp. 15–21, 1997.

Zheng–Hui He, et al., a Cell Wall–Associated, Receptor–Like Protein Kinase, The Journal of Biological Chemistry, vol. 271, No. 33, pp. 19789–19793, 1996.

Qing Yan Liu, et al., A Gametophyte Cell Wall Protein Of The Red Alga Porphyra Purpurea (Rhodophyta) Contains Four Apparent Polysaccharide–Binding Domains, J. Phycol. vol. 32, pp. 995–1003, 1996.

Qing Yan Liu, et al., A Sporophyte Cell Wall Protein Of The Red Alga Porphyra Purpurea (Rhodophyta) Is a Novel Member Of The Chymotrypsin Family . . . J. Phycol. vol. 32, pp. 1003–1009, 1996.

Ludwig, Martha et al., High Molecular Mass Glycoproteins Associated With The Siliceous Scales And Bristles Of Mallomonas Splendens . . . , Planta (1996) 199: 219–228.

Rzepecki, Leszek M., and J. Herbert Waite, Wrestling The Muscle From Mussel Beards: Research and Applications, Molecular Marine Biology and Biotechnology (1995) 4(4):313–322.

PLANT PROTEINS

FIELD AND BACKGROUND OF THE INVENTION

The present invention relates to adhesive proteins which have been isolated from mature plants such as algae. The isolated proteins may be but are not necessarily, those utilized by the plants for adhesion to substrates. The invention also relates to a process for isolating such proteins.

Algae are known as commercial sources of food and polysaccharides such as agar, alginates, carrageenan and furcellaran. Many such polysaccharides possess adhesive properties and are therefore used as gums and adhesives, and in wound dressings.

Apart from the existing industrial practice of extracting polysaccharide gums from algae, interest has been shown in algae and other plants as a source for pharmaceuticals or compounds which are otherwise bioactive, as well as in the means and adhesive substances by which algae and other plants, including certain bacteria and fungi, adhere to substrates in nature.

Walker, G. in Chapter 5 of "Synthetic Adhesives and Sealants", ed. Wake, W. C., publ. Society of Chemical Industry, 1987, page 117, mentions that in macroalgae the adhesives used by spores and the rhizoid disc adhesives are polysaccharide-protein complexes, while filamentous rhizoid adhesive is a complex polysaccharide only. This reference also mentions (page 117) that in *Laminaria digitata,* mucilage with a high phenolic content —apparently contained in tannins—plays a role in cementing the rhizoid to the substrate, the presence of phenolic compounds possibly leading to hardening of the cement (c.f. barnacle and mussel adhesion, and see below) and renders the cement/substrate bond immune to growth of microorganisms; and at page 118, in connection with microalgae, it is reporter that the adhesive of *A. veneta* is composed of a complex polysaccharide and that no protein or lipid was detected.

It is known that proteins which appear to serve chiefly as waterproof adhesives and varnishes in nature, are widely distributed throughout the animal kingdom. In particular, the chemical and physical stability of such materials is believed to be imparted thereto by quinone tanning of polyphenolic proteins, implying that their desirable waterproof/adhesive properties is due to catechol oxidase-catalyzed oxidation of a structural unit in the protein derived from 3,4-dihydroxyphenyl-L-alanine (DOPA) to a corresponding 2-(3,4-dioxo-3,4-dihydrobenzyl)glycine unit, which is then capable of undergoing numerous reactions, such that the potential adhesives and varnishes would be cured. (See, e.g., "The Phylogeny and Chemical Diversity of Quinone-Tanned Glues and Varnishes", Waite, J. H., Comp. Biochem. Physiol., 97B(1): 19–29 (1990)). In this connection, it has been noted, e.g., in an article by Saez, C. et al, Comp. Biochem, Physiol., 98B(4): 569–72 (1991) that polyphenolic adhesive proteins extracted from three species of marine mussels contain 7.9–17.4% DOPA; two of the three species contain 13.1–17.4% DOPA and 17.8–18.8% of the basic aminoacid lysine.

However, the general differences between the animal and plant kingdoms are fairly well known. Plant cell walls are usually polysaccharidic in nature and plants are usually non-motile, feed by absorption and/or photosynthesis, and can synthesize aminoacids, and thus proteins. Animal cell membranes are by contrast not polysaccharidic, and animals feed by digestion and do not generally photosynthesize.

Wagner, V. T., et al, in P.N.A.S. (USA) 89: 3644–3648 (1992), described a vitronectin-like glycoprotein (Vn-F) isolated from zygotes and two-celled embryos, which were in turn propagated from material obtained from reproductive fronds of *Fucus distichus.* Vn-F is said to be exclusively localized in the cell wall of the rhizoid tip, at the site of contact between the Fucus embryo and its substrate. This article appears to imply a parallelism between the structure and function of Vn-F in Fucus embryos, and that of vitronectin (Vn) in mammals which together with other extracellular matrix (ECM) proteins are linked structurally and functionally through the plasma membrane to the cytoskeleton via a family of transmembrane proteins. This article also mentions briefly that a Vn-like protein was isolated from the acellular slime mold Physarum, but this mention does not refer to adhesion. The authors indicate that their data suggest evolutionary conservation of structure and function of Vn between brown algae and mammals. However, this suggestion has not found ready acceptance in the field, because, inter alia, similarity of functions between "Vn-like" proteins and animal vitronectins has not been confirmed. For example, Zhu, J.-K. et al in The Plant Cell. 6: 393–404 (1994) posit the possibility that plant Vn-like proteins have little or no primary sequence identity with animal vitronectin. It may also be noted in passing that although vitronectins and vitronectin-like proteins are referred to as "adhesion proteins", the adhesion in question so far as proteins of animal origin are concerned, appears to be principally adhesion within an organism, whereas such proteins of plant origin may exhibit additionally adhesion to substrates, e.g. in the case of algae.

SUMMARY OF THE INVENTION

It is an object of the present invention to provide adhesive proteins which are distinct from polyphenolic adhesive proteins. Other objects of the invention will appear from the description which follows.

Thus, in one aspect, the invention provides adhesive proteins isolated from mature plants, particularly mature algae, the proteins being characterized by the presence of at least one ROD (Arg-Gly-Asp) or RGD-like (e.g. Arg-Tyr-Asp)) or other adhesive recognition sequence, the absence of DOPA and hydroxyproline units, and by the fact that the proteins may be used by the plants in their natural state, for the purpose of adhesion to substrates. In another aspect, the adhesive proteins isolated from mature plants are characterized by the property that they interfere with the adhesion of T-cells to an extracellular matrix such as fibronectin and/or laminin, as well as by the absence of DOPA and hydroxyproline units.

In still another aspect, the invention provides tissue adhesive proteins isolated from mature algae, and characterized by the property that they interfere with the adhesion of T-cells to an extracellular matrix selected from fibronectin and laminin, and by the absence of DOPA and hydroxyproline units. To the best of the inventor's knowledge, the adhesive proteins of the invention have never before been isolated.

The present adhesive proteins are characterized, in a particular embodiment, by an average aminoacid analysis as follows: an aspartate content is 10.5 to 13.0 mol %; a glycine content of more than 9 mol % and an alanine content of more than 7.6 mol %, provided that the total (glycine +alanine) content is no more than 23.5%; a glutamate content of 9.0 to 12.0 mol %; and a cystine content of 0.85 to 1.15 mol %. In this context and throughout the specification and claims, the "average amino acid analysis" is based on total aminoacids therein excepting tryptophan.

Where the context permits, and when not otherwise qualified, the term "algae" in the present specification and claims means both macroalgae and microalgae.

DETAILED DESCRIPTION OF THE INVENTION

The proteins according to the invention are characterized inter alia (i) by the absence of DOPA, which distinguishes them from polyphenolic proteins, e.g. those isolated from mussels and other sessile invertebrates; and (ii) by the absence of hydroxyproline, thus distinguishing them from cell-wall proteins in plants.

The proteins according to the invention are further preferably characterized by an average amino acid analysis including an aspartate content of 10.5 to 13.0 mol %, and particularly (in addition) a glycine content of more than 9 mol % and an alanine content of more than 7.6 mol %, provided that the total (glycine+alanine) content is no more than 23.5%. To the best of the inventor's knowledge, these characteristics distinguish the present proteins from vitronectius of known aminoacid composition (c.f. Kitngaki-Ogawa, H. et al, Biochimica et Biophysica Acta, 1033: 49–56 (1990)); however, the possibility should not be excluded that, notwithstanding the stated difference in aminoacid composition the present proteins, the latter might be immunologically (and perhaps biologically and biochemically) classifiable as vitronectin-like proteins, in case they react with antibodies to animal vitronectins. Also, the present proteins are distinguished particularly by their high aspartate content, e.g., from the microalgae biomass of which the aminoacid composition was reported by Brown M. R. J., J. Exptl. Marine Biol. Ecol., 145: 79–99 (1991) and by Brown M. R. et al, J. Exptl. Marine Biol. Ecol., 1.61: 91–113 (1992); however, a further point of distinction is that most of these microalgae contain the aminoacids hydroxyproline and ornithine, which are absent from the present proteins.

Preferably, the proteins according to the invention are yet further characterized by a glutamate content of 9.0 to 12.0 mol %, and/or by a cystine content of 0.85 to 1.15 mol %, or both.

The following classification scheme for algae will be utilized herein. Included in prokaryota are the algae divisions Cyanophycota and Prochlorophycota. Included in Eukaryota are the algae divisions Rhodophycota, Chromophycota, Euglenophycota and Chlorophycota.

Without prejudice to the generality of the invention, the mature algae may be selected from the classes Chrysophyceae, Prymnesiophyceae, Xantliophyceae, Eustigmatophyceae, Bacillariophyceae, Dinophyceae, Phaeophyceae, Raphidophyceae and Cryptophyceae of the division Chromophycota. It will be apparent, however, that other classes and species of mature algae, and microalgae generally, may be utilized for the purposes of the invention, e.g. such other classes and species as are exemplified, infra.

Thus, in general terms, the invention applies to adhesive proteins obtained from all tissues of mature algae, including such algae which utilize adhesive vesicles for adhesion to a substrate, and to mature microalgae, and the invention thus applies particular to all such mature algae and microalgae of any species, within divisions, classes, sub-classes, orders, families and genuses of algae and microalgae, including any unclassified species, as well as to any mixtures of algae and/or microalgae.

Without detracting from the generality of the preceding paragraph, the mature algae may be selected from the order Dictyotales, within the class Phaeophyceae, e.g. of the species Padina Pavonia Gaillon. Examples of other orders within this class are Ectocarpales, Cutleriales, Sporochnales, Sphacelariales and Fucales.

It may be noted in passing that the algae divisions Rhodophycota, Chromophycota, and Chlorophycota include what are more commonly known as red, brown and green algae, respectively, and that these three divisions more or less correspond to, or at least include, what are known in other classifications as Rhodophyta, Phaeophyta and Chlorophycota, respectively.

In an adhesive vesicle, it may be noted in relation to the present invention, that adhesive proteins therein will, of necessity, adhere generally both to cells at the appropriate algal surface and to a substrate external to the algae which could be, e.g., stones, rocks, earthenware, glass, metal or plastic objects, bone, live animal cells, cells in other growing plants, dead plants, and wood including wooden objects), and that the adhesive proteins of the invention are not those which are unique for adhesion in, e.g., specific symbiotic or parasitic relationships. Whatever the mechanism of adhesion relating to adhesive substances in adhesive vesicles may be in any particular case, it will of course be appreciated that the fact that adhesive proteins may be extracted from such vesicles means that the adhesive function of the adhesive proteins present therein has not been exhausted by in situ adhesion.

It now appears to be fairly well-established that, in nature, the presence in adhesive proteins of adhesive recognition sequences, consisting of fairly short peptide sequences, is at least in part responsible for the attachment of the proteins to cell surface receptors, particularly integrins (see e.g. Yamada, K. M., J. Biol. Chem., 266(20): 12809–12812 (1991)). Accordingly, in a particular embodiment of the invention, the proteins which are the subject of the invention are characterized additionally by the fact that they contain at least one adhesive recognition sequence.

The above description will facilitate a better understanding of the various embodiments of the invention which are set forth below.

In a particular embodiment, the adhesive proteins of the invention are additionally characterized by at least one of the following features: it contains at least one adhesive recognition sequence; based on total aminoacids therein excepting tryptophan, its aspartate content is 10.5 to 13.0 mol %; and/or the mature plants are selected from macroalgae and microalgae. Preferably also, the following features (a) and/ or (b) apply to the adhesive protein of the invention:

(a) based on total aminoacids in the adhesive proteins excepting tryptophan, the aspartate content is 10.5 to 13.0 mol %, and the aminoacid composition of the proteins may also be characterized by at least one of the following features: a glycine content of more than 9 mol % and an alanine content of more than 7.6 mol %, provided that the total (glycine+alanine) content is no more than 23.5%; and/or a glutamate content of 9.0 to 12.0 mol %; and/or a cystine content of 0.85 to 1.15 mol %;

(b) the mature plants are macroalgae or microalgae, selected from the algae divisions Cyanophycota, Prochlorophycota, Rhodophycota, Chromophycota, Euglenophycota and Chlorophycota.

In a particular embodiment, the adhesive proteins of the invention are isolatable by a process which includes the sequential steps of: extracting material selected from tissues of mature algae, holdfast or adhesive vesicle material utilized by mature macroalgae for adhesion to substrates, arid microalgae, in presence of an aqueous medium to give a supernatant and an insoluble residue; subjecting the insoluble residue to an aqueous treatment in presence of surface active agent, at a temperature between 0° and 10° C., whereby the proteins are extracted into the aqueous phase; and separating the aqueous phase containing the proteins.

Preferably above-described process, at least one of the following features also apply: extraction is effected after or simultaneously with comminution of the material; the medium is an aqueous salt solution; the aqueous treatment is an acidic treatment; the aqueous treatment is carried out in presence of antioxidant; the aqueous treatment is carried out in presence of enzyme inhibitor; the protein-containing separated aqueous phase is subjected to the further step of precipitating the protein therefrom by a technique selected from addition of a solvent (e.g. acetone) in which the protein is insoluble, and salting-out the protein. Note that sodium bisulfite exemplifies a compound which combines both antioxidant and enzyme inhibitor.

It will be appreciated that the above-defined process, at least as applied, to isolation of the adhesive proteins of the invention, is itself both novel and inventive.

The present invention moreover provides adhesive proteins isolated from mature plants, wherein the proteins may be used in nature for adhesion of the plants to substrates, the aminoacids of the proteins being characterized by the absence of DOPA and hydroxyproline, and by having an average aminoacid composition, based on total aminoacids in the adhesive protein excepting tryptophan, as follows: an aspartate content is 10.5 to 13.0 mol %; a glycine content of more than 9 mol % and an alanine content of more than 7.6 mol %, provided that the total (glycine+alanine) content is no more than 23.5%; a glutamate content of 9.0 to 12.0 mol %; and a cystine content of 0.85 to 1.15 mol %.

The invention will now be illustrated by the following non-limiting Examples, in which Examples 1–relate to isolation of proteins from algal holdfast material and Examples 5–9 relate to isolation of proteins from the whole tissue material of algae.

EXAMPLE 1

(a) A sample of the seaweed species Padina Pavonia Gaillon, which occurs in sea water of the Mediterranean coast of Israel, was detached from its rock substrate together with the holdfast (including vesicle material), which was then cut from the detached plant and stored in a freezer at −18° C. 25 g of the frozen pad was comminuted in a blender with 250 ml 1M NaCl for five minutes at ambient temperature. The mixture was centrifuged for five minutes at 5000 G, and the residue was collected and comminuted in a blender for ten minutes at 4° C., with a solution (denoted solution A) of 250 ml acetic acid (5%), containing also NaHSO$_3$ (1 mM) and Tween 80 (0.1%).

(b) The resultant mixture from (a) was centrifuged for ten minutes at ambient temperature and 5000 G, and the supernatant was collected.

(c) The protein was separated from the supernatant in part (b) by adding acetone (2 vols, precooled to −20° C.), leaving overnight at −20° C., centrifugation (5000 G. 4° C., 20 minutes), and freeze-drying the solid residue; the dry product contained 6.0 wt. % protein, on the basis of aminoacid analysis. Its aminoacid constitution (except tryptophan, not determined) is shown in the following Table, which also compares specific aminoacid content of a number of prior art proteins.

| AMINO-ACID | PROTEIN OF THE INVENTION (RESIDUES/1000) | WT. % | PRIOR *Vn (RESIDUES/1000) | ART ♥poly- phenolic | PROTEINS ♣ micro- algae WT. % |
|---|---|---|---|---|---|
| Aspartate | 117.18 | 12.692 | 89–120 | 21–42+ | 7.1–10.1♦ |
| Threonine | 59.18 | 5.630 | | | |
| Serine | 60.53 | 4.960 | | | |
| Glutamate | 100.49 | 12.207 | 100–160 | 14–23+ | 9.4–12.4 |
| Proline | 60.02 | 5.486 | | | |
| Glycine | 115.66 | 6.211 | 63–90 | ♣ | 5.1–7.5 |
| Alanine | 99.31 | 6.643 | 59–76+ | ♣ | 6.2– |
| Cystine | 9.95 | 0.928 | 2–14 | 0♦ | 0.38–1.9 |
| Valine | 69.63 | 6.497 | | | |
| Methionine | 17.87 | 2.206 | | | |
| Isoleucine | 44.68 | 4.759 | | | |
| Leucine | 64.41 | 6.861 | | | |
| Tyrosine | 35.24 | 5.412 | | | |
| Phenylalanine | 38.27 | 5.301 | | | |
| Histidine | 14.50 | 1.872 | | | |
| Lysine | 51.09 | 6.163 | | | |
| Arginine | 41.98 | 6.171 | | | |
| Ornithine | 0 | 0 | 0 | 0 | 0.1–3.9+♦ |
| Hydroxyproline | 0 | 0 | 0 | ♣ | 0.0–2.18+♦ |
| DOPA | 0 | 0 | 0 | 79–174♦ | 0 |

Key to Table: *Vn = vitronectins, Kitagaki-Ogawa, H., et al, loc cit
♥Saez, C. et al, loc cit: ♣3 mussel proteins contained
respectively 39♦, 84♦, 427♦ glycine, ⎫ residues
72♦, 50♦, 128♦ alanine, ⎬ per
122♦, 74♦, 0, hydroxyproline(s) ⎭ 1000
♣both J. Exptl. Marine Biol. Ecol. articles, loc cit: data refers to aminoacids in biomass, not in specific proteins
♦differences from present protein deemed significant

EXAMPLE 2

Starting with holdfast including vesicle material from Hypnea Musciformis Lamouroux (Hypneaceae-Gigartinales), and proceeding as described in Example 1, except that 10 g algal vesicle material and 100 ml solutions were used (instead of 25 g and 250 ml) and that the first centrifugation was carried out for 10 minutes rather than 5 minutes, dry acetone-insoluble material was isolated, which contained 14.1 wt. % protein (Lowry method using BSA as standard).

EXAMPLE 3

Starting with holdfast including vesicle material from Pterocaldia Capillaceae Bornet (Gelidiaceae–Gelidiales), and proceeding as described in Example 2, dry acetone-insoluble material was isolated, which contained 12.5 wt. % protein (Lowry method using BSA as standard).

EXAMPLE 4

Starting with holdfast including vesicle material from Laurencia Papillosa Greville (Rhodomelaceae–Ceramiales), and proceeding as described in Example 2, dry acetone-insoluble material was isolated, which contained 3.3 wt. % protein (Lowry method using BSA as standard).

EXAMPLE 5

Frozen microalgae paste (from Chlorella sp.; 60 g) was extracted with 300 ml 1M aqueous NaCl solution, while stirring with a magnetic stirrer at ambient temperature for 10 minutes, followed by centrifugation at 5000 G for 5 minutes. The supernatant was discharged and the residue was comminuted in a blender with 60 ml of an aqueous solution (solution C) containing 5% acetic acid, 0.5% sodium bisulfite, 0.5% sodium lauryl sulfate (SLS) and 0.1% Tween 80, for 10 minutes at 4° C. The solution was centrifuged for 10 minutes at 4° C. and 5000 G. As described in part (c) of Example 1, dry product was isolated from the supernatant; its protein content was 40 wt. % (Lowry method using BSA as standard).

Tests on products of Examples 4 and 5

(1) The product under test was suspended, in 1, 5 or 10% concentration, in saline solution, and the suspension was used to attempt to adhere together two pieces of mouse skin taken from Balb/c male mice, in the form of touching annuli in a Petrie dish, at their point of contact. In one series of experiments, the two pieces of skin to which the suspension had been applied were immersed together in saline solution; under these conditions, no adhesion was obtained. In another series of experiments, the two pieces of skin to which the suspension had been applied were allowed to stand in air, in a Petrie dish. Under these conditions, after several weeks, the Example 4 product, and a mixture of the Examples 4 and 5 products, at 10% concentration, both gave good adhesion (i.e. resistance to mechanical separation), and the Example 5 product alone gave fairly good adhesion at 5% or 10% concentration.

(2) When the tests in the preceding paragraph were repeated in vivo, in an attempt to transplant skin from B57 male mice onto Balb/c male mice, no adhesion occurred after about 3 weeks. However, the treated mice suffered no ill-effects from the products of Examples 4 and 5, and it may thus be inferred that these products are both bioabsorbable and biocompatible.

(3) In accordance with the procedure outlined in Biochimica et Biophysica Acta, 812: 98–103 (1986), 20 mg of each product were dissolved in 0.2 ml of 0.2M phosphate buffer containing 100 mM ascorbic acid, using a micro tissue grinder method; to some samples were added mushroom Tyrosinase (Sigma) at a final concentration of 1 mg/ml. The samples were vortexed and incubated at 37° C. over a weekend, with constant bubbling of air therethrough. All samples gelled; there was no essential difference between the samples which included or excluded Tyrosinase. The gelling of these products is consistent with their adhesive characteristics. While this method does not show the presence or absence of DOPA, the absence of DOPA has been shown elsewhere herein, by amino acid analysis.

(4) For the purpose of further purification, and in accordance with the procedure of "method B" described in Methods in Enzymology, 228: 671 (1994), a solution of 1.5 parts by weight (pbw) of a 1:1 mixture of the products of Examples 1and 5 in 100 parts by volume (pbv) was mixed at ambient temperature for 15 minutes with a solution of 15 pbw K$_2$CO$_3$ in 100 pbv water, then 20 pbw polyethylene glycol (PEG 1550) was added and the whole was stirred for a further 15 minutes and then subjected to low-speed centrifugation. This operation resulted in two phases, each of which was treated after separation with 3×the volume of acetone giving precipitates which were suspended in distilled water, dialyzed against distilled water, reprecipitated as before and freeze-dried. These purified fractions were then subjected to a T-cell competitive adhesion test (without quenching) as detailed in Alon, R. et al., Eur. J. Immunol., 1993, 23: 893–898, with the following results:

| T-CELL ADHESION TEST RESULTS | | | | |
|---|---|---|---|---|
| | top phase | fraction | bottom phase | fraction |
| concentration (µg/ml) | 4 | 80 | 40 | 800 |
| adhesion as % of control: | | | | |
| fibronectin | 93 | 89 | 78 | 72 |
| laminin | | 95 | | 38 |

These results indicate generally that the present adhesive proteins interfere with the adhesion of T-cells to an extracellular matrix; and that the purified inventive product in the top fraction contains at least one RGD or RGD-like adhesive recognition sequence, while that in the bottom fraction interferes with T-cell adhesion not exclusively because it contains an RGD or RGD-like adhesive recognition sequence.

EXAMPLE 6

Frozen microalgae paste #3 (90 g) was processed as described in Example 5, except that 90 ml solution C was used. The protein content of the dry product was 36 wt. %.

EXAMPLE 7

Dried *Spirulina maxima* powder (10 g) was processed as described in Example 5, except that 200 ml salt solution and 120 ml solution C were used. The protein content of the dry product was 19 wt. %.

EXAMPLE 8

Nori sheets (25 g) are comminuted and extracted with 400 ml 1M aqueous NaCl solution, while stirring with a magnetic stirrer at ambient temperature for 10 minutes, followed by centrifugation at 5000 G for 5 minutes. The supernatant was discharged and the residue was comminuted in a blender with 300 ml of an aqueous solution containing 5% acetic acid, 0.3% sodium bisulfite and 0.1% Tween 80, for 10 minutes at 4° C. The solution was centrifuged for 10 minutes at 4° C. and 5000 G. As described in part (c) of Example 1, dry product was isolated from the supernatant; its protein content was 30 wt. % (Lowry method using BSA as standard). (As is known in the art, Nori consists of Porphyra and/or Monostroma.)

EXAMPLE 9

Nori sheets (5 g) are comminuted and extracted twice with 100 ml M aqueous NaCl solution, while stirring with a magnetic stirrer at ambient temperature for 10 minutes, followed by centrifugation at 5000 G for 5 minutes. The supernatant was discharged and the residue was comminuted in a blender with 150 ml of an aqueous solution containing 5% acetic acid, 0.3% sodium bisulfite, 0.1% SLS and 0.1% Tween 80, for 10 minutes at 4° C. The solution was centrifuged for 10 minutes at 4° C. and 5000 G. As described in part (c) of Example 1, dry product was isolated from the supernatant; its protein content was 40 wt. %.

It is believed that the extracted proteins of the present invention could find application in the fields of adhesives and varnishes, particularly as tissue adhesives for medical and dental applications, e.g. in healing of wounds, as well as in drug delivery systems.

While the present invention has been particularly described with respect to its presently preferred embodiments, it will be appreciated by skilled persons that many modifications and variations may be made. Merely by way of illustration, the protein(s) may be isolated by processes including features which are the mechanical and/or chemical equivalents of the particularly described processes. Moreover, it will be apparent that the proteins extracted from plant sources (or their analogs) could be chemically synthesized or genetically engineered. Consequently, it will be appreciated that the invention is not to be construed as restricted to the particularly described embodiments, rather regard will be had to the concept, spirit and scope of the invention, in the light of the present disclosure and the claims which follow.

I claim:

1. Adhesive proteins which possess the following characteristics:
   (a) said adhesive proteins have been isolated from the holdfast of mature macroalgae;
   (b) said adhesive proteins do not contain hydroxyproline units;
   (c) said adhesive proteins do not contain 3,4-dihydroxyphenyl-L-alanine (DOPA) units;
   (d) said adhesive proteins interfere with the binding of T-cells to an extracellular matrix;
   (e) said adhesive proteins are insoluble in water when water is use as an extraction medium extract proteins from said holdfast of mature macroalgae; and
   (f) said adhesive proteins may be used by said mature macroalgae, in the natural state of said mature macroalgae, to adhere to a substrate.

2. Adhesive proteins according to claim 1, wherein said extracellular matrix is selected from the group consisting of fibronectin and laminin.

3. Adhesive proteins according to claim 1, wherein said adhesive proteins contain an adhesive recognition sequence.

4. Adhesive proteins according to claim 3, wherein said adhesive recognition sequence is selected from the group consisting of arginine-glycine-aspartate and arginine-tyrosine-aspartate.

5. Adhesive proteins according to claim 3, wherein said adhesive recognition sequence is an RGD-like sequence.

6. Adhesive proteins according to claim 1, wherein said mature macroalgae are selected from the macroalgae divisions Rhodophycota, Chromophycota and Chlorophycota.

7. Adhesive proteins according to claim 1, wherein based on total aminoacids therein excepting tryptophan, the average aminoacid analysis is characterized by an aspartate content in the range of 10.5 to 13.0 mol %.

8. Adhesive proteins according to claim 7, wherein the average aminoacid analysis is further characterized by a glycine content of more than 9 mol % and an alanine content of more than 7.6 mol %, provided that the total (glycine+alanine) content is no more than 23.5%; a glutamate content of 9.0 to 12.0 mol %; and a cysteine content of 0.85 to 1.15 mol %.

9. Adhesive proteins according to claim 1, which are characterized by an average aminoacid analysis as follows: an aspartate content of 10.5 to 13.0 mol %; a glycine content of more than 9 mol % and an alanine content of more than 7.6 mol %, provided that the total (glycine+alanine) content is more than 23.5%; a glutamate content of 9.0 to 12.0 mol % and a cysteine content of 0.85 to 1.15 mol %.

10. Adhesive proteins according to claim 9, wherein said macroalgae are selected from the macroalgae divisions Rhodophycota, Chromophycota and Chlorophycota.

11. Adhesive proteins according to claim 1, wherein said adhesive proteins are tissue adhesive proteins, and said extracellular matrix is selected from the group consisting of fibronectin and laminin.

12. Adhesive proteins which possess the following characteristics:
    (a) said adhesive proteins have been isolated from the holdfast of mature macroalgae;
    (b) said adhesive proteins do not contain hydroxyproline units;
    (c) said adhesive proteins do not contain 3,4-dihydroxyphenyl-L-alanine (DOPA) units;
    (d) said adhesive proteins contain at least one adhesive recognition sequence;
    (e) said adhesive proteins may be used by said mature macroalgae, in the natural state of said mature macroalgae, to adhere to a substrate; and
    (f) said adhesive proteins are insoluble in water when water is used as an extraction medium to extract proteins from said holdfast of mature macroalgae.

13. Adhesive proteins according to claim 12, wherein the adhesive recognition sequence is selected from the group consisting of arginine-glycine-aspartate and arginine-tyrosine-aspartate.

14. Adhesive proteins according to claim 12, further characterized in that they inhibit the binding of T-cells to an extracellular matrix selected from the group of fibronectin and laminin.

15. Adhesive proteins according to claim 14, wherein the adhesive recognition sequence is an RGD-like sequence.

16. Adhesive proteins according to claim 12, wherein said macroalgae are selected from the macroalgae divisions Rhodophycota, Chromophycota and Chlorophycota.

17. Adhesive proteins according to claim 12, wherein based on total aminoacids therein excepting tryptophan, the average aminoacid analysis is characterized by an aspartate content in the range of 10.5 to 13.0 mol %.

18. Adhesive proteins according to claim 17, wherein the average aminoacid analysis is further characterized by a glycine content of more than 9 mol % and an alanine content of more than 7.6 mol %, provided that the total (glycine+alanine) content is no more than 23.5%; a glutamate content of 9.0 to 12.0 mol %; and a cysteine content of 0.85 to 1.15 mol %.

19. Adhesive proteins according to claim 12, which are characterized by an average aminoacid analysis as follows: an aspartate content in the range of 10.5 to 13.0 mol %; a glycine content of more than 9 mol % and an alanine content of more than 7.6 mol %, provided that the total (glycine+alanine) content is no more than 23.5%; a glutamate content of 9.0 to 12.0 mol %; and a cysteine content of 0.85 to 1.15 mol %.

20. Adhesive proteins according to claim 19, wherein said macroalgae are selected from the macroalgae divisions Rhodophycota, Chromophycota and Chlorophycota.

* * * * *